United States Patent
Luque Vera et al.

(10) Patent No.: US 10,426,859 B2
(45) Date of Patent: Oct. 1, 2019

(54) DEVICE FOR RELEASING VOLATILE SUBSTANCES

(71) Applicant: ZOBELE ESPAÑA, S.A., Barcelona (ES)

(72) Inventors: Sergio Luque Vera, Barcelona (ES); Dominic Doyle, Barcelona (ES); Chao Hsu Lee, Barcelona (ES)

(73) Assignee: ZOBELE ESPAÑA, S.A., Barcelona (ES)

( * ) Notice: Subject to any disclaimer, the term of this patent is extended or adjusted under 35 U.S.C. 154(b) by 0 days.

(21) Appl. No.: 15/537,507

(22) PCT Filed: Dec. 10, 2015

(86) PCT No.: PCT/ES2015/070891
§ 371 (c)(1),
(2) Date: Jun. 19, 2017

(87) PCT Pub. No.: WO2016/097437
PCT Pub. Date: Jun. 23, 2016

(65) Prior Publication Data
US 2017/0340767 A1    Nov. 30, 2017

(30) Foreign Application Priority Data
Dec. 17, 2014    (ES) .................................. 201431860

(51) Int. Cl.
*B01F 3/04* (2006.01)
*A61L 9/12* (2006.01)
(Continued)

(52) U.S. Cl.
CPC .................................... *A61L 9/12* (2013.01); *A61L 9/04* (2013.01); *B01F 3/04028* (2013.01); *B05B 7/0081* (2013.01); *A61L 2209/111* (2013.01)

(58) Field of Classification Search
CPC .......... A61L 9/12; B01F 3/04; B01F 3/04099; B01F 3/0407; B01F 3/04028; B01F 3/04021
(Continued)

(56) References Cited

U.S. PATENT DOCUMENTS

| 6,103,201 A | 8/2000 | Green ........................ 422/124 |
| 6,764,656 B1 | 7/2004 | Matulevich ................. 422/124 |

(Continued)

FOREIGN PATENT DOCUMENTS

| WO | WO 01/66158 A1 | 9/2001 |
| WO | WO 2005/030277 A1 | 4/2005 |
| WO | WO 2010/070576 A1 | 6/2010 |

OTHER PUBLICATIONS

International Search Report dated Feb. 2, 2016 in corresponding PCT International Application No. PCT/ES2015/070891.
(Continued)

*Primary Examiner* — Robert A Hopkins
(74) *Attorney, Agent, or Firm* — Ostrolenk Faber LLP

(57) ABSTRACT

A device for releasing volatile substances comprising a container containing the volatile substances located in a fixed position, and means for generating an air flow in order to release the volatile substances, the means for generating an air flow comprising a movable body, the movement of which generates the air flow; at least one magnet arranged on said movable body; and means for generating magnetic flux, the actuation of which causes the displacement of the movable body by means of the repulsion force between said at least one magnet in the movable body and the magnetic flux. The device enables energy consumption to be improved by using magnetically assisted periodic low-consumption actuation.

7 Claims, 2 Drawing Sheets

(51) Int. Cl.
  *A61L 9/04* (2006.01)
  *B05B 7/00* (2006.01)

(58) Field of Classification Search
  USPC ........................ 261/30, 83, DIG. 88; 422/124
  See application file for complete search history.

(56) References Cited

U.S. PATENT DOCUMENTS

| | | | | |
|---|---|---|---|---|
| 7,619,337 | B2 * | 11/2009 | Kasai | ........................ H02K 3/47 |
| | | | | 310/156.32 |
| 2002/0197188 | A1 | 12/2002 | Lua | ................................ 422/124 |
| 2004/0250962 | A1 | 12/2004 | Hart et al. | ......................... 159/7 |
| 2007/0036673 | A1 * | 2/2007 | Selander | ................. A61L 9/122 |
| | | | | 422/5 |
| 2010/0272615 | A1 | 10/2010 | Yang | ............................ 422/124 |

OTHER PUBLICATIONS

Written Opinion dated Feb. 1, 2016 in corresponding PCT International Application No. PCT/ES2015/070891.

\* cited by examiner

DEVICE FOR RELEASING VOLATILE SUBSTANCES

CROSS-REFERENCE TO RELATED APPLICATIONS

The present application is a 35 U.S.C. §§ 371 national phase conversion of PCT/ES2015/070891, filed Dec. 10, 2015, which claims priority to Spanish Patent Application No. P201431860, filed Dec. 17, 2014, the contents of which are incorporated herein by reference. The PCT International Application was published in the Spanish language.

TECHNICAL FIELD

The present invention relates to a device for releasing volatile substances, enabling air flow with an aroma created by a volatile substance to be generated.

BACKGROUND OF THE INVENTION

One type of air fresheners or systems for releasing volatile substances currently known is made up of a container inside of which an air-freshening product or a volatile substance is housed, which may consist of fragrances, pesticides, etc.

In the manufacturing of said air fresheners or systems for releasing volatile chemicals, said container is sealed so that the air freshener retains all of its aroma, such that when it is to be used, it is necessary to remove the seal.

One problem with these currently known air fresheners or systems for releasing volatile substances is that by simply opening a container it is possible that the desired dispersion of the aroma of said air-freshening product is not achieved.

To solve this disadvantage, systems for releasing volatile substances comprising means for generating air flow for the correct dispersion of the aroma of the air-freshening product are known, for example fans, heaters, atomizers, nebulizers, aerosols or passive evaporation elements.

Currently existing solutions have different disadvantages, such as excessively high energy consumption, in the case of heaters, which generally require connection to the electrical grid to meet the required energy needs.

In the case of atomizers, nebulizers and fans, energy consumption is more moderate, and allows for the use of batteries, but they have a disadvantage in that they require frequent and regular battery replacement. Furthermore, these types of devices also have the disadvantage of their difficulty, or lack of regulation regarding the regulation of the release rate intensity.

Another disadvantage of fans and sprayers is the noise they produce when releasing volatile substances, which may be bothersome to the user.

Therefore, a first objective of the present invention is to provide a system for releasing volatile substances, which allows for a proper release of volatile substances at the lowest possible energy consumption.

DESCRIPTION OF THE INVENTION

The device for releasing volatile substances of the invention resolves the aforementioned drawbacks and has other advantages, which are described below.

The device for releasing volatile substances according to the present invention comprises a container containing the volatile substances located in a fixed position and means for generating an air flow in order to release the volatile substances, and is characterized in that said means for generating an air flow comprise:
  a movable body, the movement of which generates the air flow;
  at least one magnet arranged on said movable body; and means for generating magnetic flux, the actuation of which causes the displacement of said movable body by means of the repulsion force between the at least one magnet on the movable body and said magnetic flux.

Furthermore, said means for generating magnetic flux are arranged in the vicinity of the movable body in at least one of the positions of said movable body and comprise a detector, which actuates the generation of magnetic flux by detecting the magnet, or one of the magnets of said movable body.

According to an embodiment, said movable body is a sheet, which swivels with respect to a shaft, and the magnet is preferably arranged on the movable body on the end opposite to the swivel end.

According to another embodiment, said movable body comprises a plurality of rotating sheets with respect to a central shaft, and said movable body comprises a plurality of magnets arranged near the outer part of each sheet.

According to a preferred embodiment, said means for generating magnetic flux comprise an induction coil which is powered by means of one or more batteries.

The device for releasing volatile substances according to the present invention provides, at least, the following advantages:
  it enables energy consumption to be improved by using magnetically assisted periodic low-consumption actuation. This periodic actuation facilitates the low energy consumption, extending the useful life of the batteries;
  it provides a continuous release of the volatile substances through the use of membranes, gels, waxes, impregnated solids, etc.;
  it allows the intensity of the release of volatile substances to be adjusted by adjusting some of the movement variables of the container containing volatile substances, such as the swivel range, the frequency, the rotational speed, etc.

BRIEF DESCRIPTION OF THE DRAWINGS

For the purpose of helping to make the foregoing description more readily understandable, it is accompanied by a set of drawings that, schematically and by way of illustration and not limitation, represent an embodiment.

DESCRIPTION OF A PREFERRED EMBODIMENT

Figure 1:
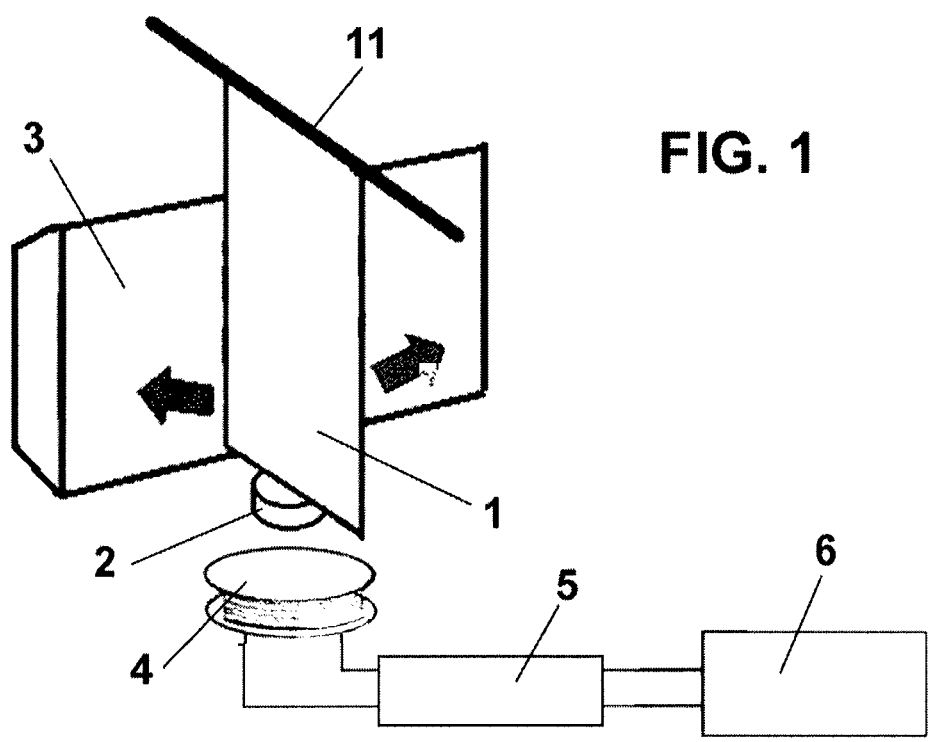
FIG. 1 is a side elevation view of the device for releasing volatile substances of the present invention, according to a first embodiment.

FIG. 1 shows a first embodiment of the device for releasing volatile substances according to the present invention.

According to this embodiment, the volatile substances are contained in a container 3, which is in a fixed position, and air flow is produced for the release thereof by means of a movable body 1 located in front of said container 3.

It must be indicated that the volatile substances may be aromatic substances for perfuming the environment or insecticide substances or any adequate substances, and the container may comprise membranes, gels, waxes, impregnated solids, etc. for the proper release of the volatile substances.

In this first embodiment, the movable body 1 is a sheet which swivels with respect to a shaft 11 arranged on one of the ends thereof, comprising a magnet 2 on the lower end thereof (according to the represented embodiment).

Said movable body 1 is secured to the shaft 11 in order to swivel at the upper end thereof, such that the movable body 1 will move as shown by means of the arrows in FIG. 1.

The device according to the present invention also comprises means for generating magnetic flux, comprising an induction coil 4 located in the vicinity of the magnet 2 when the movable body 1 is located in a vertical position, according to the embodiment shown.

The induction coil 4 is connected to a circuit 5, which functions as a detector to detect the proximity of said magnet 2, and also to one or more batteries 6 for powering the magnetic flux generating means.

As can be seen in FIG. 1, the induction coil 4 is located on the lower part, and when the movable body 1 is located in a vertical position, said induction coil 4 is actuated by the circuit 5 when the proximity of the magnet 2 is detected, generating magnetic flux that repels the magnet 2, causing the swivel motion of the movable body 1.

This swivel motion of the movable body 1 facilitates the release of volatile substances by generating air flow, and the device according to the present invention uses the majority of its energy at moment the induction coil 4 is activated.

Figure 2:
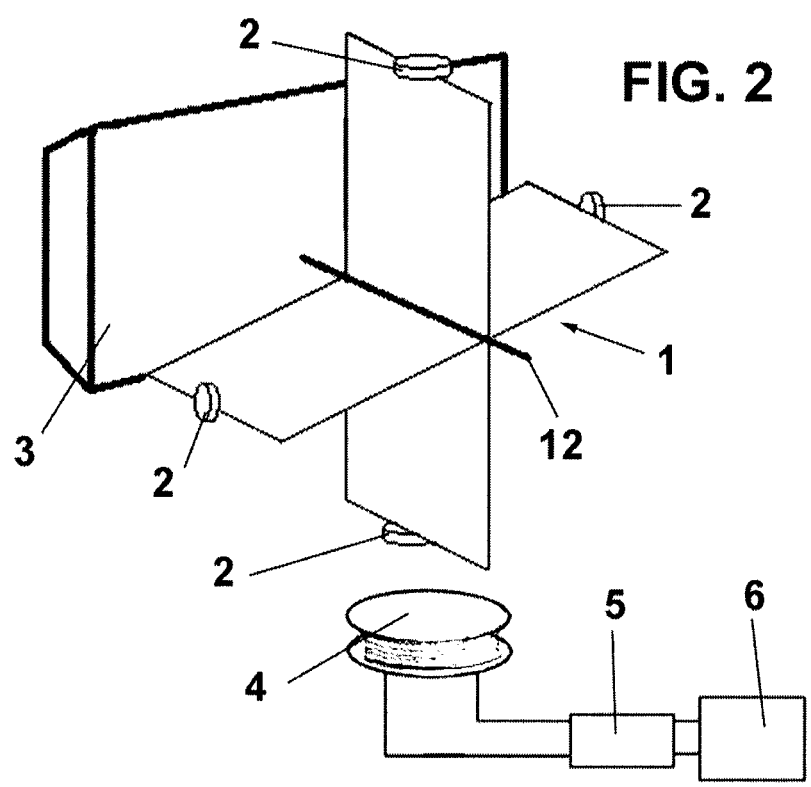
FIG. 2 is a side elevation view of the device for releasing volatile substances of the present invention, according to a second embodiment.

FIG. 2 shows a second embodiment of the device according to the present invention.

It must be noted that in order to facilitate the description of the device, the same numerical references have been used to indicate the same or equivalent elements to those of the first embodiment.

In this embodiment, the main difference with respect to the previous embodiment is that the movable body 1 comprises a plurality of sheets, four in the embodiment represented, which are rotational with respect to a central shaft 12.

In this embodiment, the device according to the present invention also comprises an induction coil 4, a circuit 5 and one or more batteries 6, the operation of which is the same as in the previous embodiment. In this case, however, the movable body 1 will describe a rotational motion around the central shaft 12, and not a swivel motion, as in the case of the previous embodiment.

These embodiments may be adjusted or improved in the following way:

Energy efficiency may be improved by using a larger induction coil or a stronger magnet, varying the swivel range, adjusting the current, adjusting the balance point, varying the pivot point or varying the total weight of the device.

Although reference has been made to a specific embodiment of the invention, it is evident for a person skilled in the art that numerous variations and changes may be made to the described device for releasing volatile substances, and that all the aforementioned details may be substituted by other technically equivalent ones, without detracting from the scope of protection defined by the attached claims.

The invention claimed is:

1. A device for releasing volatile substances comprising a container containing the volatile substances located in a fixed position and means for generating an air flow in order to release the volatile substances, wherein said means for generating an air flow comprise:

a movable body, the movement of which generates the air flow, wherein said movable body is a sheet which swivels with respect to a shaft;

at least one magnet arranged on said movable body on an end opposite to the swivel end of said sheet; and means for generating magnetic flux the actuation of which causes the displacement of said movable body by the repulsion force between said at least one magnet on the movable body and said magnetic flux.

2. The device for releasing volatile substances according to claim 1, wherein said means for generating magnetic flux are arranged in the vicinity of the movable body in at least one of the positions of said movable body.

3. The device for releasing volatile substances according to claim 1, wherein said means for generating magnetic flux comprise a detector which actuates the generation of magnetic flux by detecting the magnet or one of the magnets of said movable body.

4. The device for releasing volatile substances according to claim 1, wherein said movable body comprises a plurality of rotating sheets with respect to a central shaft.

5. The device for releasing volatile substances according to claim 4, wherein said movable body comprises a plurality of magnets arranged near the outer part of each sheet.

6. The device for releasing volatile substances according to claim 1, wherein said means for generating magnetic flux comprise an induction coil.

7. The device for releasing volatile substances according to claim 6, wherein said induction coil is powered by one or more batteries and controlled by a circuit.

* * * * *